United States Patent [19]

Mitchell et al.

[11] Patent Number: 5,197,636

[45] Date of Patent: Mar. 30, 1993

[54] FAST ACTIVATION CHLORINE DIOXIDE DELIVERY APPARATUS

[75] Inventors: David W. Mitchell, Orange; John Baker, Irvine; Hampar Karageozian, Laguna Hills; Daniel F. Smith, Irvine, all of Calif.

[73] Assignee: Allergan, Inc., Irvine, Calif.

[21] Appl. No.: 830,387

[22] Filed: Feb. 3, 1992

[51] Int. Cl.$^5$ .............................................. B67D 5/58
[52] U.S. Cl. ................... 222/190; 222/212; 222/129; 134/901; 252/187.21; 514/840
[58] Field of Search ............... 222/190, 189, 129, 145, 222/206, 207, 212, 215, 420, 548, 554, 555, 519-525; 206/5.1, 219; 134/901; 514/840; 215/6; 423/275, 477; 422/28, 30; 424/661-663, 429, 616; 252/186.1, 187.21

[56] References Cited

U.S. PATENT DOCUMENTS

| | | | |
|---|---|---|---|
| Re. 23,218 | 4/1950 | Levy | 162/87 |
| Re. 32,672 | 5/1988 | Huth et al. | 252/95 |
| 2,436,134 | 2/1948 | Aston | 423/477 |
| 2,761,833 | 9/1956 | Ward | 222/189 X |
| 3,123,521 | 3/1964 | Wentworth | 424/615 |
| 3,189,223 | 6/1965 | Mackal | 222/189 X |
| 3,278,447 | 10/1966 | McNicholas | 252/186.21 |
| 3,591,515 | 7/1971 | Lovely | 252/186.22 |
| 3,819,828 | 6/1974 | McCoy | 424/71 |
| 3,910,296 | 10/1975 | Karageozian et al. | |
| 3,912,451 | 10/1975 | Gaglia, Jr. | 422/30 |
| 4,011,941 | 3/1977 | Parsons | 206/5.1 |
| 4,084,747 | 3/1978 | Alliger | 422/20 |
| 4,104,190 | 8/1978 | Hartshorn | 252/187.21 |
| 4,123,376 | 10/1978 | Gray | 252/99 |
| 4,456,510 | 6/1984 | Murakami | 204/101 |
| 4,459,217 | 7/1984 | Bogie | 252/99 X |
| 4,499,077 | 2/1985 | Stockel et al. | 424/661 |
| 4,557,925 | 12/1985 | Lindahl et al. | 424/482 |
| 4,568,517 | 2/1986 | Kaspar et al. | 422/30 |
| 4,614,549 | 9/1986 | Ogunbuyi et al. | 422/28 X |
| 4,618,444 | 10/1986 | Hudson et al. | 252/92 |
| 4,654,208 | 3/1987 | Stockel et al. | 424/78.08 |
| 4,689,215 | 8/1987 | Ratcliff | 424/53 |
| 4,690,773 | 9/1987 | Ogunbuyi et al. | 252/174.12 |
| 4,767,559 | 8/1988 | Kruse et al. | 252/106 |
| 4,792,442 | 12/1988 | Ratcliff | 424/53 |
| 4,855,135 | 8/1989 | Ratcliff | 424/661 |
| 4,947,986 | 8/1990 | Ballu | 222/145 X |
| 4,997,626 | 3/1991 | Dziabo et al. | 422/37 |
| 5,013,459 | 5/1991 | Gettings et al. | 514/840 |
| 5,056,689 | 10/1991 | Heyl et al. | 222/190 X |
| 5,078,908 | 1/1992 | Ripley et al. | 252/187.21 |
| 5,105,993 | 4/1992 | La Haye et al. | 222/189 |

FOREIGN PATENT DOCUMENTS 0082798 6/1983 European Pat. Off.
0147100 7/1985 European Pat. Off.

(List continued on next page.)

OTHER PUBLICATIONS

Chemical Abstracts Selects: Issue 2, 1987.
Eudragit L Data Sheet (Info L-2/e).

Primary Examiner—Kevin P. Shaver
Attorney, Agent, or Firm—Frank J. Uxa; Gordon L. Peterson

[57] ABSTRACT

An apparatus for dispensing a liquid medium containing dissolved chlorine dioxide comprises a reservoir which defines a receptacle adapted for holding a precursor liquid medium having chlorine dioxide precursor dissolved therein and a tip assembly into which the precursor liquid medium passes after the precursor liquid exits the receptacle. The tip assembly comprises a chamber in which is located a promoter component effective to promote the generation of chlorine dioxide from the chlorine dioxide precursor in the liquid medium present in the chamber, an outlet providing a path for the liquid medium containing dissolved chlorine dioxide to exit the chamber, and an isolation assembly acting to effectively separate the precursor liquid medium in the reservoir from the promoter when it is desired that the precursor liquid medium from the reservoir be separated from the catalyst.

30 Claims, 4 Drawing Sheets

FOREIGN PATENT DOCUMENTS

| | | |
|---|---|---|
| 0168253 | 1/1986 | European Pat. Off. . |
| 0196075 | 1/1986 | European Pat. Off. . |
| 0199385 | 10/1986 | European Pat. Off. . |
| 0209071 | 1/1987 | European Pat. Off. . |
| 0279401 | 2/1988 | European Pat. Off. . |
| 0255041A1 | 5/1988 | European Pat. Off. . |
| 0278224 | 8/1988 | European Pat. Off. . |
| 889973 | 9/1953 | Fed. Rep. of Germany ...... 222/190 |
| 3626082A1 | 11/1988 | Fed. Rep. of Germany . |
| 878694 | 1/1943 | France ................... 222/190 |
| 998154 | 1/1952 | France ................... 222/190 |
| 1230610 | 9/1960 | France ................... 222/190 |
| 531062 | 7/1955 | Italy ..................... 222/190 |
| WO85/04107 | 9/1985 | PCT Int'l Appl. . |
| WO86/05695 | 10/1986 | PCT Int'l Appl. . |
| 1269677 | 4/1982 | United Kingdom . |
| 2139260A | 11/1984 | United Kingdom . |
| 2173017A | 10/1986 | United Kingdom . |
| 2187748A | 9/1987 | United Kingdom . |
| 2151039A | 7/1988 | United Kingdom . |

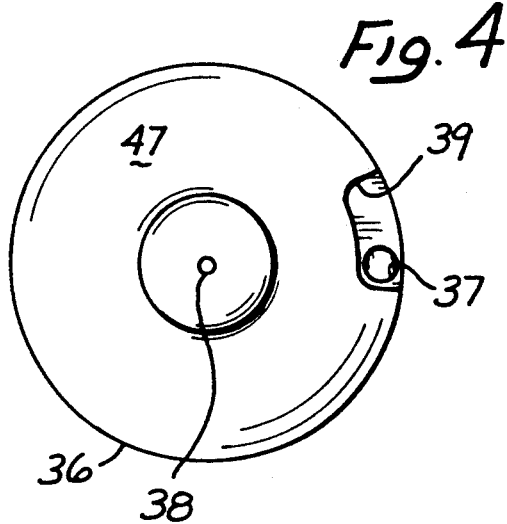
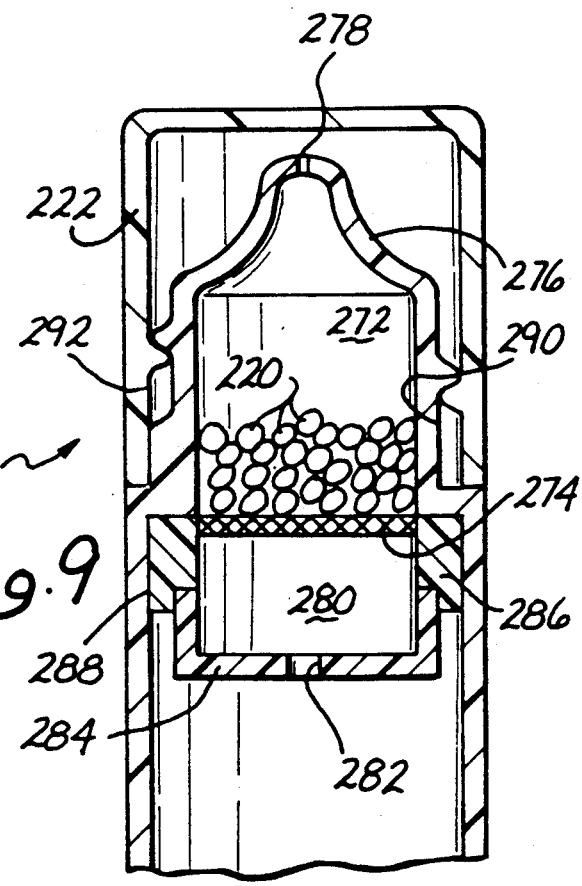
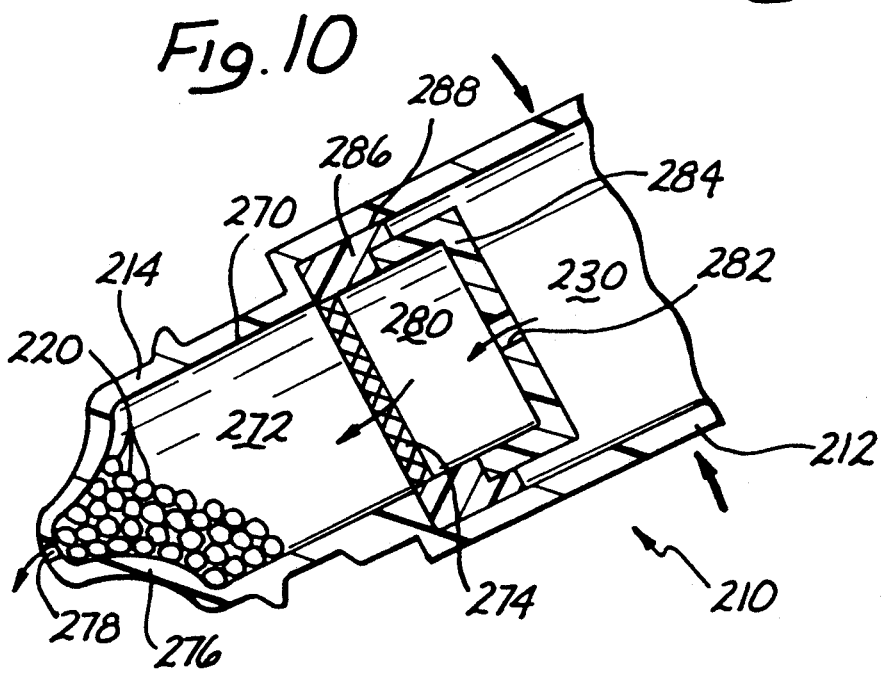

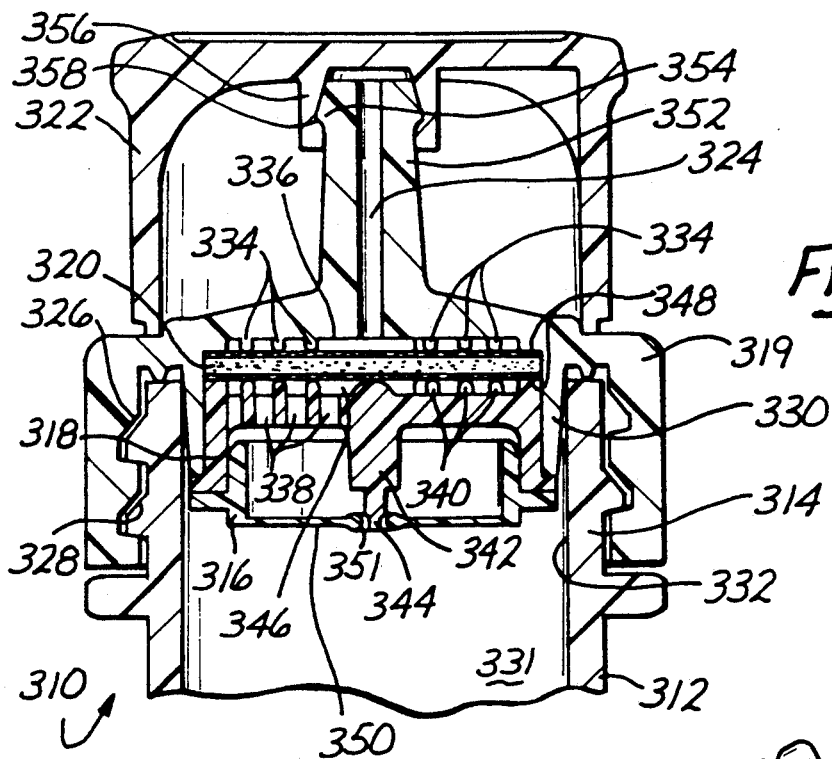
Fig. 11
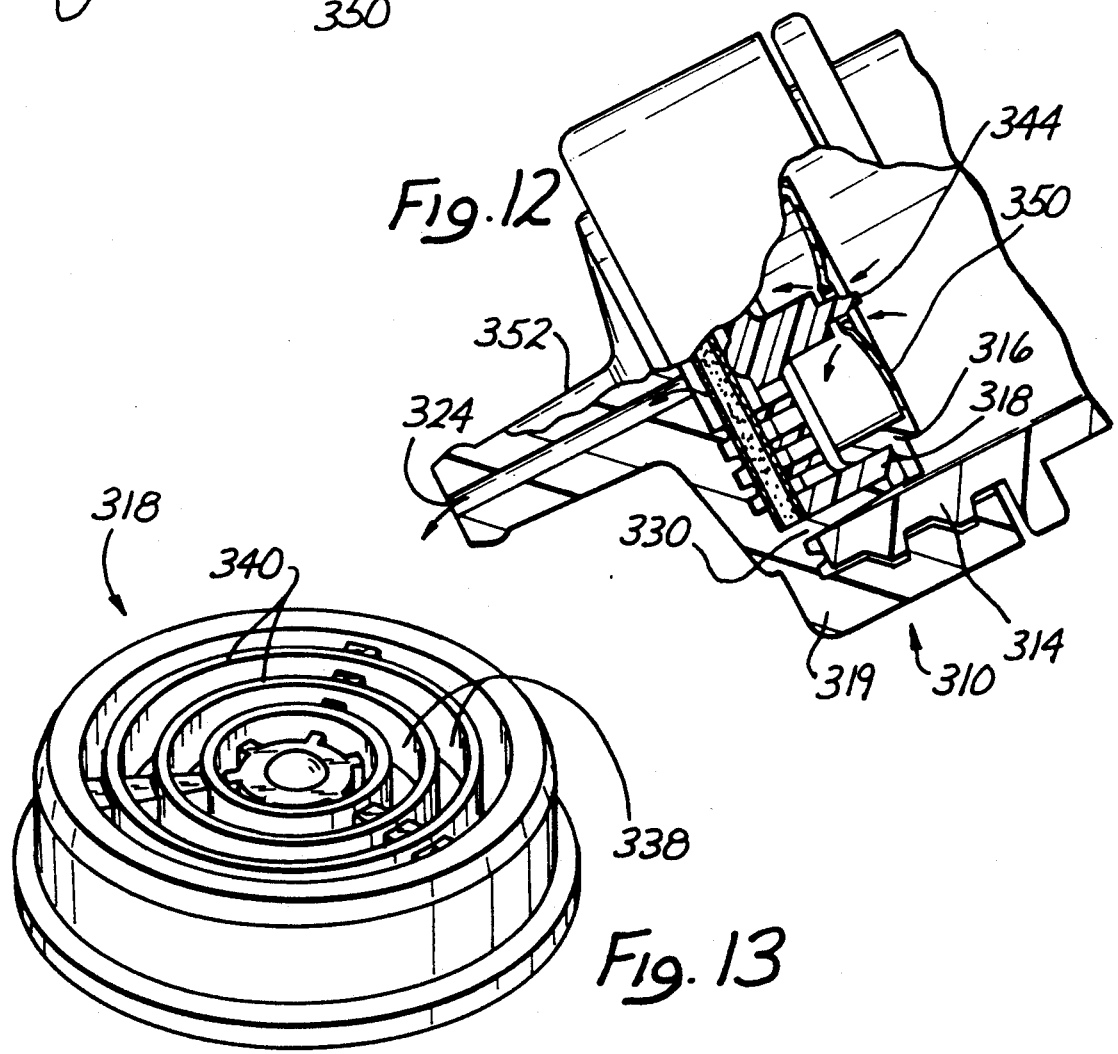
Fig. 12
Fig. 13

FAST ACTIVATION CHLORINE DIOXIDE DELIVERY APPARATUS

BACKGROUND OF THE INVENTION

This invention relates to an apparatus for the delivery of a liquid medium containing chlorine dioxide. More particularly, the invention relates to an apparatus for the delivery of a liquid medium containing chlorine dioxide derived by rapidly activating a liquid medium containing chlorine dioxide precursor with a metal component.

The use of chlorine dioxide dissolved in an aqueous liquid medium to disinfect substrates, such as contact lenses, has previously been suggested. One problem with such disinfection methods is that chlorine dioxide has relatively limited stability so that chlorine dioxide prepared well in advance of its use becomes ineffective as a disinfectant.

One approach to overcoming this problem is to use a liquid medium containing a chlorine dioxide precursor, such as stabilized chlorine dioxide. This liquid medium is subjected to the action of a transition metal component present in the same container with the contact lens to be disinfected. The transition metal component activates or promotes the chlorine dioxide precursor to generate chlorine dioxide which disinfects the contact lens. One difficulty that exists with this approach is that one or more contaminants, for example, tear proteins, associated with a contact lens to be disinfected may cause the transition metal component to become ineffective over time to promote the generation of chlorine dioxide.

Therefore, it would be advantageous to generate chlorine dioxide from a chlorine dioxide precursor without exposing the metal component to an environment containing the substrate, for example, the contact lens, to be disinfected.

SUMMARY OF THE INVENTION

A new apparatus for delivering or dispensing a liquid medium containing chlorine dioxide has been discovered. The present apparatus provides for rapid activation of chlorine dioxide precursor in a liquid medium, preferably an aqueous liquid medium, to generate a liquid medium containing a disinfecting amount of chlorine dioxide. This apparatus generates the liquid medium containing chlorine dioxide separate and apart from the substrate, for example, a contact lens, to be disinfected so that the apparatus is unaffected by the substrate and has no substantial effect on the substrate. In addition, the apparatus effectively prevents the generation of excessive amounts of chlorine dioxide-containing liquid medium. In this manner, only the desired amount of chlorine dioxide-containing liquid medium is produced and chlorine dioxide precursor-containing liquid medium is effectively prevented from forming chlorine dioxide until desired.

In one broad aspect of the present invention, an apparatus for delivering a liquid medium containing chlorine dioxide comprises a reservoir defining a receptacle for holding a precursor liquid medium having chlorine dioxide precursor located therein; and a tip assembly into which the precursor liquid medium passes after exiting the receptacle. The tip assembly includes a chamber in which is located promoter component effective to promote the generation of chlorine dioxide from the chlorine dioxide precursor present in the chamber. An outlet provides a path for the liquid medium containing chlorine dioxide to exit the chamber. The present system further includes isolation means acting to effectively separate the precursor liquid medium in the receptacle from the promoter component when it is desired that the precursor liquid medium in the receptacle be separated from the promoter component.

Using the present apparatus, the desired amount or quantity of liquid medium containing a disinfecting amount of chlorine dioxide can be generated and passed to a container where disinfection occurs, such as a lens container where contact lens disinfection occurs. At the same time the promoter component is maintained separate and apart from the disinfection site so that the substrate, e.g., contact lens, to be disinfected has no effect on the promoter component. Further, the precursor liquid medium in the receptacle is effectively separated or isolated from the promoter component so that little or no premature or unwanted generation of chlorine dioxide is obtained. Thus, the precursor liquid medium in the receptacle is maintained in a ready or unaltered state until needed for disinfection purposes.

Methods for dispensing or delivering a liquid medium containing chlorine dioxide, preferably containing dissolved chlorine dioxide, utilizing apparatus as disclosed herein are within the scope of the present invention.

DETAILED DESCRIPTION OF THE INVENTION

The present invention involves an apparatus useful for delivering a liquid medium containing chlorine dioxide, preferably a contact lens disinfecting amount of chlorine dioxide. The present apparatus includes a reservoir defining a receptacle for holding a precursor liquid medium, preferably an aqueous liquid medium including chlorine dioxide precursor, preferably dissolved chlorine dioxide precursor, therein; and a tip assembly into which the precursor liquid medium passes after the precursor liquid medium exits the receptacle. The tip assembly includes a chamber in which is located promoter component, in particular including a transition metal component, effective to promote the generation of chlorine dioxide from the chlorine dioxide precursor in the liquid medium present in the chamber. An outlet is included to provide a flow path for the liquid medium containing chlorine dioxide to exit the chamber.

The present apparatus includes isolation means acting to effectively isolate the precursor liquid medium in the receptacle from the promoter component when it is desired to separate the liquid medium in the receptacle from the promoter component.

In one embodiment, the isolation means includes a first component having a first inlet orifice in fluid communication with the receptacle, and a second component having a second inlet orifice in fluid communication with the chamber. The first and second components are moveable, for example, in the longitudinal direction and/or rotatable, relative to each other so that the first and second inlet orifices can be aligned or non-aligned, as desired. In one embodiment, the apparatus includes an assembly, preferably located on the first component and/or the second component, to restrict or limit the movement of the first and second components relative to each other. When the first and second inlet orifices are aligned, together they form a flow path for the precursor liquid medium to pass from the receptacle to the chamber. When the first and second inlet orifices are nonaligned, the receptacle is effectively separated from the chamber so that the precursor liquid medium in the receptacle is effectively isolated or separated from the promoter component in the chamber. The first component may include more than one first inlet orifice and the second component may include more than one second inlet orifice. The number of first inlet orifices and second inlet orifices are preferably the same. Each of the first inlet orifices is preferably positioned on the first component so as to be aligned or non-aligned with a second inlet orifice on the second component so that the chamber can be in fluid communication with or isolated from the receptacle, as desired.

The outlet of the present apparatus is preferably located in the second component. In one embodiment, the second component includes a top surface and the apparatus further comprises a cap adapted to be removably secured over the outlet and, preferably to substantially surround the top surface of the second component. The cap is preferably adapted so as to contact the top surface of the second component so that the second component rotates in response to rotation of the cap. In a particularly useful embodiment, at least one of the top surface of the second component and the surface of the cap that contacts the top surface of second component is textured, for example roughened, to increase the ability of the cap to grip the top surface of the second component relative to employing a second component and/or cap with corresponding surface or surfaces which are smooth.

The reservoir preferably includes an outlet port in which at least a portion of the first component and at least a portion of the second component are located. The outlet port preferably includes an outer surface which is threaded. In this embodiment, the apparatus preferably further comprises a cap adapted to be removably threaded onto the outer surface of the outlet port to effectively cover the outlet.

Alternately, the isolation means includes at least one orifice in fluid communication with the receptacle and the chamber. This at least one orifice is such as to prevent the flow of precursor liquid medium from the receptacle therethrough when the orifice is subjected to only liquid pressure from the precursor liquid medium in the receptacle. In other words, the orifice is structured and/or configured so that precursor liquid medium will not flow from the receptacle through the orifice without the imposition of an external force. This feature is highly beneficial so that even if the precursor liquid medium in the receptacle is placed in a position directly above the at least one orifice, no liquid will flow from the receptacle. The structure and configuration of the orifice depends, for example, on the surface tension of the precursor liquid medium and/or the size and configuration of the receptacle. For any given precursor liquid medium and receptacle configuration, the structure and/or size of the orifice or orifices which function as described herein can be determined by routine experimentation. In this embodiment, the reservoir is preferably sufficiently flexible so that upon application of hand pressure to the reservoir and receptacle, along with liquid pressure from the precursor liquid medium in the receptacle, precursor liquid medium from the receptacle is caused to pass through the at least one orifice.

The apparatus including an at least one orifice as described above preferably further comprises a secondary chamber in fluid communication with both the chamber and the orifice. This secondary chamber has a diameter larger than that of the at least one orifice and is substantially free of the promoter component. This secondary chamber acts to provide a space where liquid medium which has already contacted the promoter component can be located, for example, in between uses of the present apparatus to dispense liquid medium containing chlorine dioxide. This apparatus preferably further comprises an inlet in fluid communication with both the chamber and the secondary chamber. This inlet is structured to allow free flow of liquid medium between the chamber and the secondary chamber. This inlet more preferably includes one or more flow orifices each of which is sized sufficiently large to allow free flow of liquid medium between the chamber and the secondary chamber. The present apparatus may be constructed from any suitable material of construction or combination of materials of construction. Such material or materials of construction should have no substantial adverse effect on the functioning of the present apparatus, on the precursor liquid medium or on the substrate being disinfected. One or more polymeric materials are particularly useful in constructing one or more components of the present apparatus.

In yet another embodiment, the present isolation means includes a flexible membrane which is deformable by the application of deforming pressure thereto, for example by the application of human hand pressure to the reservoir and to the liquid medium in the reservoir. This flexible, deformable membrane is located between the receptacle and the chamber, and includes an orifice, preferably a centrally located orifice, therethrough. A rigid pin-like element is provided which is substantially stationary relative to the chamber and which extends into the orifice when no deforming pressure is applied to the membrane. When no deforming pressure is applied to the membrane, the membrane/pin-like element combination effectively prevents or substantially inhibits liquid medium from the receptacle from flowing past the flexible membrane and entering into the chamber. When deforming pressure is applied to the membrane, the membrane and pin-like element are adapted and structured to allow liquid medium from the receptacle past the membrane and into the chamber. Preferably, at least over a limited range of deforming pressures, the volume rate at which liquid is allowed to enter the chamber is maintained relatively constant, more preferably varies by no more than about 20%, as the deforming pressure is varied.

In this embodiment, the promoter component is preferably located in a bed, preferably a fixed or substantially stationary bed, of particles in the chamber. It is particularly useful to employ a shallow bed of particles which is more wide than it is deep, for example, at least about 2 times or at least about 5 times as wide as it is deep. This allows for effective catalyst/precursor liquid medium contacting, while at the same time reducing the pressure drop through the bed of particles. At least one filter element is preferably located adjacent a side of the bed of particles, preferably in contact with the bed of particles, and acts to hold the bed of particles in place in the chamber. More preferably, one such filter element is located adjacent the bottom or upstream side of the bed and another such filter element is located adjacent the top or downstream side of the bed.

The apparatus preferably further comprises a distributor component structured and adapted to facilitate the flow of liquid medium from the receptacle through the bed of particles. Such a distributor component is particularly useful in the situation where a shallow bed of particles is employed. In one particularly useful embodiment, the distributor component and the pin-like element are included in the same part, for example, being molded from polymeric material into a single part.

Any metal component capable of promoting the formation of chlorine dioxide from a chlorine dioxide precursor in a liquid medium, in particular in an aqueous liquid medium, preferably at a pH in the range of about 6 to about 10 or possibly higher, may be employed in the promoter component of the present invention. The preferred metal components include the transition metals and mixtures thereof, in particular selected from the metals of the following groups of the Periodic Table of Elements: Group III metals, Group IV metals, Group V metals, Group VI metals, Group VII metals, Group VIII metals and mixtures thereof.

Because of their high degree of effectiveness, platinum group metal components and mixtures thereof, preferably platinum components, palladium components, ruthenium components and mixtures thereof, and especially palladium components and mixtures thereof, are particularly useful. The platinum group metals include platinum, palladium, iridium, ruthenium, rhodium and osmium.

The metal component or components may be present in the metallic form and/or in a combined form as part of an organic or inorganic compound or complex.

The amount of metal components or components needed in the present promoter component is to be viewed in terms of what quantity is needed to generate a particular concentration of chlorine dioxide in a given time and in light of the amount of chlorine dioxide precursor present in the precursor liquid medium.

It is most convenient to place the metal component on a support. Such supports are particularly useful if the metal components include one or more platinum group metals, which are quite expensive. The support may be chosen so as to provide surface area on which the metal component or components can be placed.

Any suitable support material may be employed, and preferably is substantially inert at the conditions employed in the present invention. Examples of support materials include polymeric materials (plastics), metals, aluminas, silicas, clays, ceramics and the like. The supported transition metal component or components may have any suitable shape or configuration, such as sheets, rods, extrudates, tablets, pills, irregular shaped particulars, spheres, disks and the like. The promoter component preferably includes a plurality of particles, more preferably sized to remain in the chamber of the present apparatus. Any of a number of conventional techniques can be employed to incorporate the metal component or components in and/or on the support material. These techniques include impregnation, co-precipitation, ion-exchange, dipping, spraying, vacuum deposition, vapor deposition and the like.

The chlorine dioxide-containing liquid medium dispersed on or delivered by the present apparatus is applicable to disinfecting many substrates which are benefited by being disinfected, in particular all types of contact lenses. Such lenses may be made of any material or combination of material and may have any suitable configuration. For example, these chlorine dioxide-containing liquid media can be used to disinfect lenses made from hydrogels ("soft" lenses), lenses made from polymethyl methacrylate (PMMA), the so called "hard" lenses and other non-hydrogel gas permeable lenses. Present day examples or non-hydrogel gas permeable lens materials are organosiloxanemethacrylate polymers (Polycon® lenses), fluorocarbon polymers (Advent® lenses), cellulose acetate butyrate (CAB) materials and silicone elastomer of various compositions.

In general, such chlorine dioxide-containing liquid media contain sufficient chlorine dioxide to disinfect a given device in a given period of time. Preferably, such liquid media contain at least about 0.1 ppm, more preferably about 0.2 ppm, and still more preferably at least about 0.5 ppm, by weight of chlorine dioxide. Such amounts of chlorine dioxide, when present in solution in an aqueous liquid medium, disinfect the device, in particular the contact lens, contacting such aqueous liquid medium in about 1 to about 2 hours or less. Higher amounts of chlorine dioxide disinfect in a shorter period of time.

In general, the chlorine dioxide precursors referred to herein are compounds capable of generating, releasing or being converted to, chlorine dioxide when exposed to the promoter component, in particular to a transition metal component included in the promoter component. Among the preferred chlorine dioxide precursors useful in the present invention are chlorites and stabilized chlorine dioxide complexes. The term "stabilized chlorine dioxide" as used herein means, for example, one or more chlorine dioxide-containing complexes disclosed in U.S. Pat. Nos. 4,696,811 and 4,689,215 which are incorporated herein by reference. Chlorites include metal chlorite salts, particularly alkali metal chlorites. A specific example of a chlorite salt which is useful as a chorine dioxide precursor is sodium chlorite. Among the preferred stabilized chlorine dioxide complexes are carbonate and bicarbonate complexes. The exact chemical composition of many of these stabilized chlorine dioxide precursors is not completely understood. The manufacture or production of certain chlorine dioxide precursors is described in McNicholas U.S. Pat. No. 3,278,447, which is hereby incorporated in its entirety by reference herein. An especially useful stabilized chlorinedioxide is a product sold by BioCide International, Inc. under the trademark Purogene®.

The chlorine dioxide precursor is preferably present in the precursor liquid medium at a predetermined concentration so as to provide a disinfecting amount of chlorine dioxide in the presence of the promoter component. Preferably, the precursor liquid medium has sufficient chlorine dioxide precursor so as to have a potential of producing chlorine dioxide in a concentration of at least about 0.1 ppm by weight.

In one embodiment, the chlorine dioxide precursor includes a functionality selected from carbonate, borate, sulfate, phosphate, and mixtures thereof. Without intending to limit the scope of the present invention to any particular theory of operation, the inclusion of such groups in the chlorine dioxide precursor may correspond or be analogous to the effect of certain buffer components, as is discussed hereinafter. But the invention is fully operable without reference to a specific buffer.

The liquid medium used is selected to have no substantial detrimental effect on the substrate, e.g., contact lens, being disinfected and to allow and even facilitate the disinfection of the substrate. The liquid medium is preferably aqueous-based. A particularly useful aqueous liquid medium is that derived from saline, e.g., a conventional saline solution. Preferably the precursor aqueous liquid medium and the aqueous liquid medium containing chlorine dioxide have a pH in the range of about 6 to about 10, more preferably about 6.5 to about 8, and still more preferably about 7.5. Such more preferred and still more preferred pH ranges are substantially consistent with the normal physiological pH for humans. Thus, after disinfecting, the disinfected contact lens may be rinsed with saline or chlorine dioxide-containing liquid medium, for example, from the present system, before being placed in the eye. This is in contrast to other systems which require elaborate neutralization procedures before the lens is suitable for placement in the eye.

In order to insure that the pH of the precursor aqueous liquid medium is maintained within the desired range, the precursor aqueous liquid medium may include at least one buffer component. Although any suitable buffer component may be employed, it is preferred to select such component so as not to substantially detrimentally affect the chlorine dioxide. It is preferred that the buffer component be inorganic.

Certain buffer components actually increase or facilitate the rate and/or amount of chlorine dioxide formed from the precursor. Among these buffer components are those which include phosphate functionalities, borate functionalities, carbonate functionalities and mixtures thereof. Particularly increased rates of chlorine dioxide formation are achieved when the buffer component includes phosphate functionalities, borate functionalities and mixtures thereof. Alkali metal and alkaline earth metal buffer components are advantageously used in the present invention.

Further, in order to avoid possible eye irritation, it is preferred that the presently useful precursor liquid media have an osmolality (a measure of tonicity) of at least about 200 mOsmol/kg, preferably in the range of about 200 to about 350 or about 400 mOsmol/kg. In an especially useful embodiment, the osmolality or tonicity of the precursor liquid medium substantially corresponds to the tonicity of the fluids of the eye, in particular the human eye.

Any suitable ophthalmically acceptable tonicity component or components may be employed, provided that such component or components are compatible with the other ingredients of the precursor liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The amount of ophthalmically acceptable tonicity component utilized can vary widely. In one embodiment, the tonicity component is preferably present in the precursor liquid medium in an amount in the range of about 0.5 to about 0.9 weight/volume percent of the formulation.

Typical of ophthalmically acceptable inorganic salt tonicity components are alkali metal chlorides and alkaline earth metal chlorides, such as sodium chloride, potassium chloride, calcium chloride and magnesium chloride.

One or more additional components can be included in the presently useful precursor liquid media. Such additional component or components are chosen to impart or provide at least one beneficial or desired property to the liquid media. Such additional components may be selected from components which are conventionally used in one or more contact lens care compositions. Examples of such additional components include cleaning agents, wetting agents, nutrient agents, sequestering agents, viscosity builders, contact lens conditioning agents, antioxidants, and the like. These additional components may each be included in the precursor liquid medium in an amount effective to impart or provide the beneficial or desired property to the liquid medium. For example, such additional components may be included in the presently useful precursor liquid media in amounts similar to the amounts of such components used in other, e.g., conventional, contact lens care products.

Examples of useful wetting agents include polyvinyl alcohol, polyoxamers, polyvinyl pyrrollidone, hydroxypropyl methyl cellulose and mixtures thereof.

Examples of useful sequestering agents include disodium ethylene diamine tetraacetate, alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

Examples of useful antioxidants include sodium metabisulfite, sodium thiosulfate, N-acetylcysteine, butylated hydroxyanisole, butylated hydroxytoluene and mixtures thereof.

After being dispensed from the present apparatus, the chlorine dioxide-containing liquid medium is preferably used to disinfect a substrate, in particular a contact lens. Thus, the substrate to be disinfected is contacted with the chlorine dioxide-containing liquid medium at conditions to disinfect the substrate.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to; about 60° C. Contacting at or about ambient temperature is very convenient and useful. The contacting preferably occurs at or about atmospheric pressure. This contacting preferably occurs for a time to substantially completely disinfect the substrate being treated. When disinfecting contact lenses, such contacting times can be in the range of about 0.1 hours to about 12 hours or more. After such contacting, the disinfected contact lens may be contacted with, for example, rinsed with and/or soaked in, a substantially chlorine dioxide-free liquid medium, e.g., a conventional saline solution, to remove residual chlorine dioxide from the lens before placing the lens in the wearer's eye.

Various aspects of the present invention are illustrated in the accompanying drawings in which like parts bear like reference numbers.

BRIEF DESCRIPTION OF THE DRAWINGS

FIG. 4 is a plan view taken generally along line 4—4 of FIG. 2.

FIG. 9 is a partial cross-sectional view of a further embodiment of the present apparatus.

FIG. 10 is a partial cross-sectional view of the further embodiment of FIG. 5 shown in use dispensing chlorine-dioxide-containing liquid medium.

FIG. 11 is a partial cross-sectional view of an additional embodiment of the present apparatus.

FIG. 12 is a partial view, partly in cross-section, of the embodiment shown in FIG. 11 showing chlorine dioxide-containing liquid medium being dispensed.

FIG. 13 is a top front view, in perspective, of the distributor component of the embodiment shown in FIG. 11.

DETAILED DESCRIPTION OF THE DRAWINGS

Figure 1:
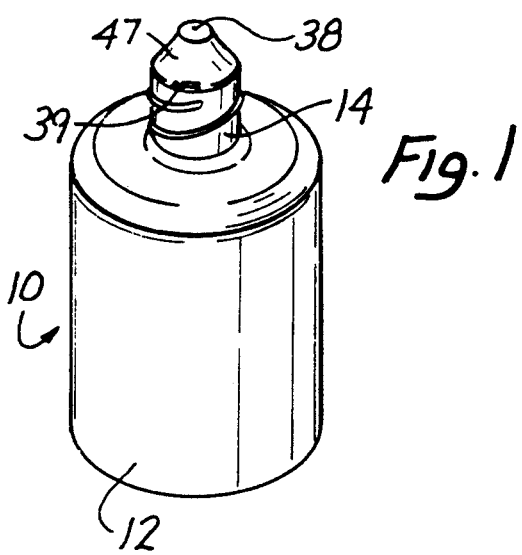
FIG. 1 is a top front view, in perspective, of an embodiment of the present apparatus.

Referring now to the drawings, FIGS. 1 to 5 illustrate a chlorine dioxide delivery apparatus or bottle, shown generally at 10, which includes a bottle body 12, a bottle stem 14, a first component 16, a second component 18, a plurality of particles 20 and a bottle cap 22. Each of the components of bottle 10, except for the plurality of particles 20, is made of a polymeric material which has no substantial detrimental effect on, and is not substantially detrimentally affected by, either the precursor aqueous liquid medium in bottle 10 or the chlorine-dioxide containing liquid medium dispensed by bottle 10. Such components may include a pigment, such as titanium dioxide, to provide a suitable, for example, white, color. Each of the components of bottle 10 can be sized appropriately to meet the requirements of the particular application involved. For example, if bottle 10 is to be used to supply chlorine dioxide-containing liquid medium for contact lens disinfecting, bottle body 12 may be sized to hold about 100 cc to about 500 cc or about 1000 cc or more of precursor liquid medium. In this embodiment, about 5 cc to about 10 cc of chlorine dioxide-containing liquid medium can be produced and dispensed to disinfect a pair of contact lenses.

First component 16 is force fitted into the opening defined by the inner surface 24 of bottle stem 14. Alternately, first component 16 may be adhesively or otherwise secured to bottle stem 14, in particular to inner surface 24 of the bottle stem. In any event, first component 16 is held stationary relative to bottle stem 14.

The first component 16 includes a depending portion 26 which includes a first inlet orifice 28 extending through first component 16. First component 16 includes a first closed end 29. First inlet orifice 28 is located in the receptacle 30 defined by bottle body 12 so that liquid, in particular, precursor aqueous liquid medium in receptacle 30, can pass into first inlet orifice 28.

Second component 18 includes an elongated portion 32 which is located within the space defined by the inner wall 34 of the first component 16. The fit between the elongated portion 32 of second component 18 and first component 16 is such that the two parts, that is the first component 16 and the second component 18, are rotatable in a limited manner relative to each other, in particular, the second component 18 is rotatable in a limited manner relative to the first component 16. The elongated portion 32 of second component 18 is snugly fit into the space defined by inner wall 34 of first component 16.

Second component 18 includes an upper portion 36 which includes an outlet orifice 38, which forms the outlet of the apparatus 10.

First component 16 includes a projection 37 which extends through an opening 39 in upper portion 36 of second component 18. The combination of projection 37 and opening 39 act to limit the rotatability of second component 18 relative to first component 16.

Figure 2:
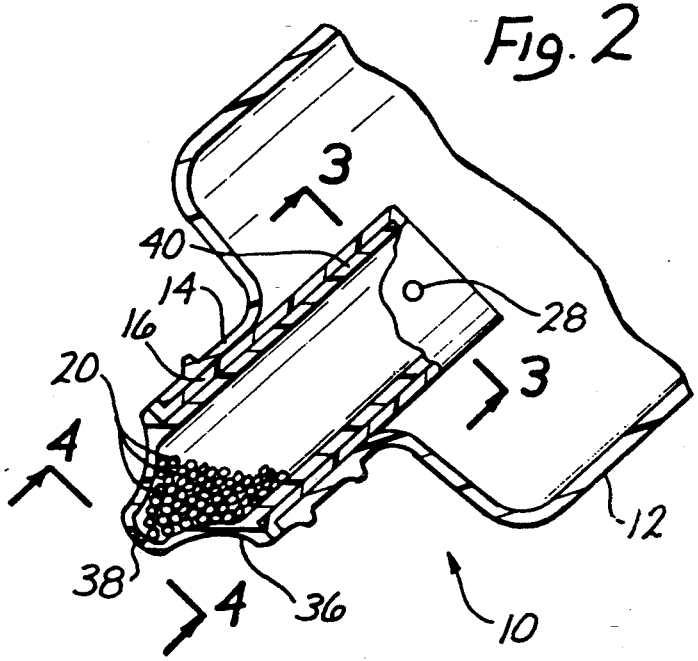
FIG. 2 is a partial cross-sectional view of the embodiment shown in FIG. 1.
Figure 3:
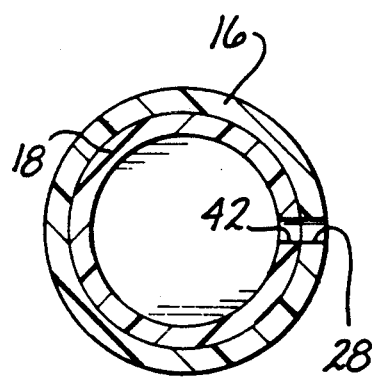
FIG. 3 is a cross-sectional view taken generally along line 3—3 of FIG. 2.
Figure 5:
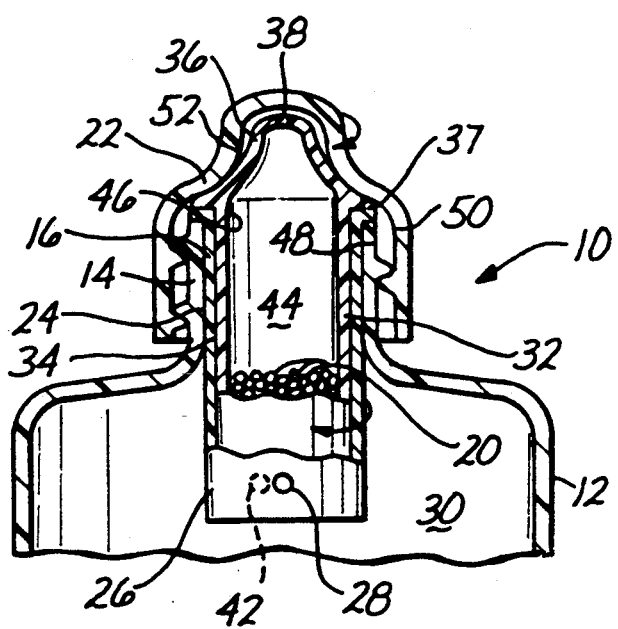
FIG. 5 is a partial cross-sectional view of the embodiment shown in FIG. 1 with a cap in place.

Second component 18 includes a depending portion 40 which substantially coincides with depending portion 26 of first component 16. Depending portion 40 includes a second inlet orifice 42 which is located at the same vertical height as first inlet orifice 28. Second inlet orifice 42 is in fluid communication with chamber 44 which is defined by the inner wall 46 of second component 18. Since second component 18 can be rotated in a limited manner relative to first component 16, second inlet orifice 42 can be rotated in a limited manner relative to first inlet orifice 28. Thus, when it is desired to have no liquid from receptacle 30 passed into chamber 44, second component 18 is rotated so that first inlet orifice 28 is not aligned with second inlet orifice 42, as shown in FIG. 4. However, when it is desired to have liquid from receptacle 30 flow into chamber 44, second component 18 is rotated so that first inlet orifice 28 and second inlet orifice 42 are aligned, as shown in FIGS. 2 and 3. This simple rotation mechanism provides an effective way to control the flow of liquid from receptacle 30 into chamber 44. The combination of projection 37 and opening 39 is positioned and sized so that the second component 18 can be rotated relative to first component 16 to the extent that inlet orifices 28 and 42 can be placed in aligned position or non aligned position as a result of this relative rotation.

The upper portion 36 of second component 18 includes a top surface 47 which may be textured, such as roughened, to facilitate the limited rotation of second component 18 relative to first component 16.

Bottle stem 14 includes an outer surface 48 which is threaded. Bottle cap 22 includes an inner surface 50 which is threaded with threads which engage the threads on outer surface 48 of bottle stem 14. By threading or unthreading bottle cap 22 onto or from bottle stem 14, the outlet 38 can be effectively covered or uncovered, as desired. Frictional contact between surface 52 of bottle cap 22 and top surface 47 of second component 18 facilitates limited rotation of the second component 18 relative to first component 16. This top inner surface 52 of bottle cap 22 can be textured, such as roughened, to facilitate frictional contact between this surface and the top surface 47 of second component 18.

The plurality of particles 20 are located in chamber 44. These particles 20 are sized so as to remain in chamber 44. That is, the particles 20 have sufficient size so as not to escape through either first and second inlet orifices 28 and 42 or outlet 38. The plurality of particles 20 include sufficient palladium, for example, about 1% or less to about 10% or more, such as, about 5% (by weight, calculated as elemental palladium) to be effective to promote the conversion of a chorine dioxide precursor in the liquid passed from receptacle 30 to chamber 44 into chlorine dioxide, in particular a contact lens disinfecting amount of chlorine dioxide. These particles may be derived using any of a number of conventional techniques for depositing platinum on a substrate. The particles may be made of polymeric material or an inorganic oxide, such as alumina, silica and the like.

Receptacle 30 includes a precursor aqueous liquid medium including chlorine dioxide precursor, in particular stabilized chlorine dioxide such as that sold under the trademark Purogene® by BioCide International, Inc. This aqueous liquid medium may contain, for example, about 0.01% to about 0.2% by weight of stabilized chlorine dioxide, and in addition an effective amount of a buffering agent, preferably a borate buffering agent, to maintain the pH of the solution in the range of about 6 to about 10. The aqueous liquid medium may be derived from a conventional saline solution. In any event, the aqueous liquid medium includes an effective amount of a tonicity agent to provide for ophthalmically acceptable tonicity.

The apparatus 10 functions as follows. When it is desired to store the apparatus 10 between uses, or during shipment, the apparatus is configured substantially as shown in FIG. 4. Thus, the first inlet orifice 28 and second inlet orifice 42 are positioned to be non-aligned and bottle cap 22 is threaded tightly onto bottle stem 14 to cover outlet 38.

When it is desired to dispense chlorine dioxide-containing liquid medium from apparatus 10, for example, to disinfect a contact lens, the following procedure is implemented. Bottle cap 22 is rotated, e.g., by hand pressure. Since top surface 52 of bottle cap 22 is in frictional contact with top surface 47 of second component 18, rotating cap 22 rotates second component 18 relative to first component 16 until stopped by projection 37 coming into contact with the walls of opening 39. This limited rotation of second component 18 relative to first component 16 results in the first inlet orifice 28 and second inlet orifice 42 being placed in aligned position, as shown in FIG. 3. The bottle cap 22 is further unthreaded from bottle stem 14 and removed from the apparatus 10. The bottle body 12 is turned, as shown in FIG. 2, to cause liquid medium from receptacle 30 to flow through aligned first inlet orifice 28 and second inlet orifice 42 into chamber 44, where this liquid medium is contacted with the plurality of particles 20. This contacting effects the rapid formation of chlorine dioxide from the chlorine dioxide precursor in the liquid medium from receptacle 30. The chlorine dioxide-containing liquid medium then passes through outlet 38 and into a lens container or other device where contact lens disinfection is to occur.

After sufficient chlorine dioxide-containing liquid medium has been delivered, the apparatus 10 is again uprighted so as to drain all of the liquid from chamber 44 back into receptacle 30. Bottle cap 22 is then threaded back onto bottle stem 14 and is squeezed so as to rotate second component 18 relative to first component 16 to place first inlet orifice 28 and second inlet orifice 42 in non-aligned position. In this manner, the apparatus 10 is ready to be stored, and is available for further use in the future.

Figure 6:
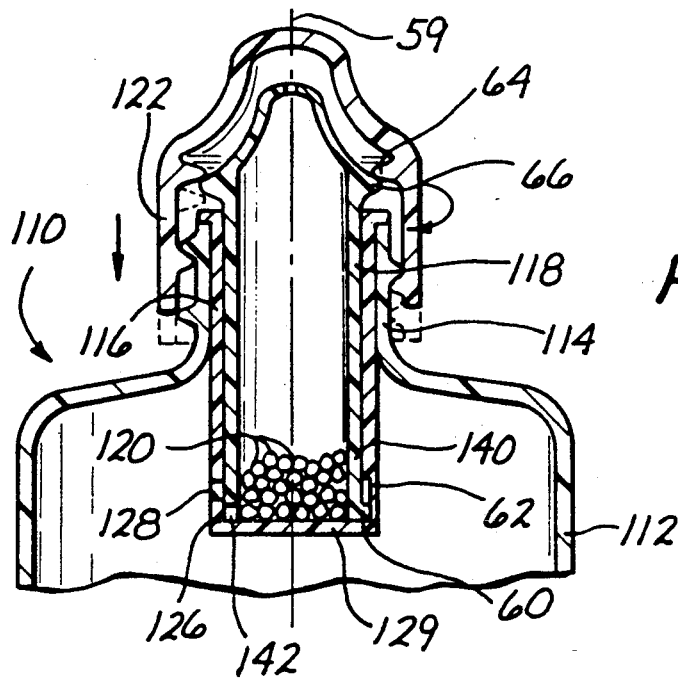
FIG. 6 is a partial cross-sectional view of an alternative embodiment of the present apparatus showing the inlet orifices in the non-aligned position.
Figure 7:
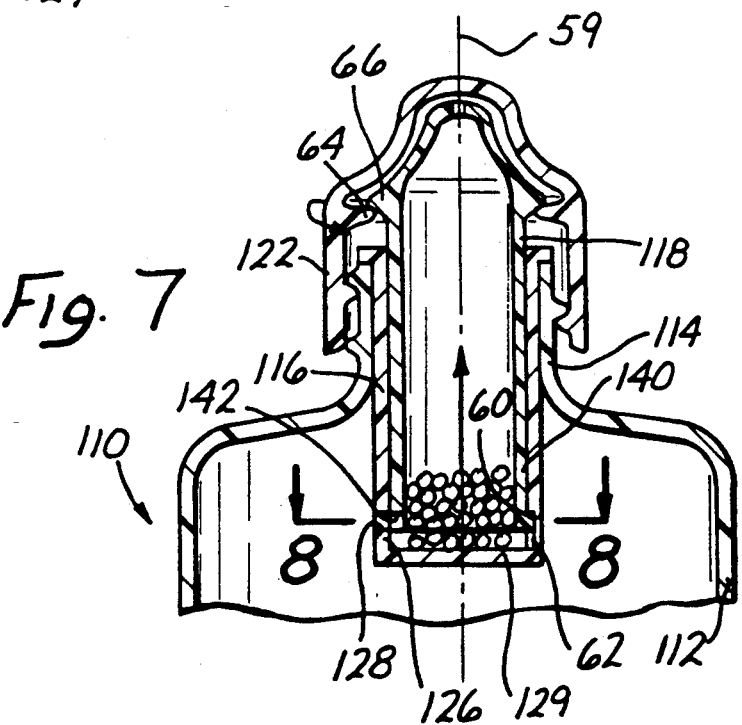
FIG. 7 is a partial cross-sectional view of the alternative embodiment shown in FIG. 6 showing the inlet orifices in the aligned position.
Figure 8:
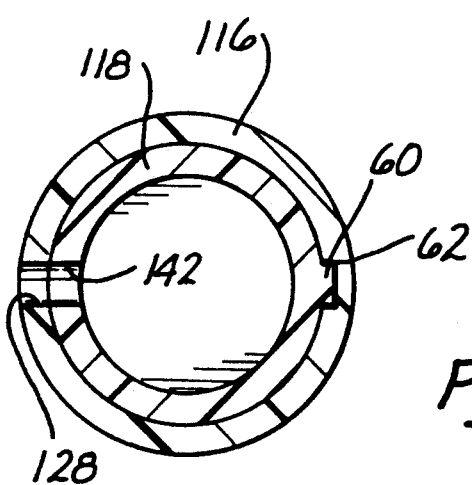
FIG. 8 is a cross-sectional view taken generally along line 8—8 of FIG. 7.

FIGS. 6, 7 and 8 illustrate an alternative embodiment of the present chlorine dioxide delivery apparatus. This alternative embodiment, shown generally at 110, includes a bottle body 112, a bottle stem 114, a first component 116, a second component 118, a plurality of particles 120 and a bottle cap 122. Except as expressly stated herein, each of the components of the alternative apparatus 110 are structured and sized, and function in a manner similar to the corresponding component of apparatus 10. The reference numerals of the corresponding components of alternative apparatus 110 are increased by 100 relative to the reference numerals of the corresponding components of apparatus 10.

The primary difference between alternative apparatus 110 and apparatus 10 is that second component 118 is restrictedly moveable in the up/down direction, that is in a direction parallel to the longitudinal axis 59 of the first and/or second component, as shown in FIGS. 6 and 7, to bring second inlet orifice 142 into and out of alignment with first inlet orifice 128. To achieve this restricted movement, the depending portion 140 of second component 118 includes a radially outwardly extending key 60, and depending portion 126 of first component 116 includes a key hole 62. Key 60 is fitted into key hole 62 so that when key 60 is positioned in the lower end of key hole 62, as shown in FIG. 6, second inlet orifice 142 is not aligned with first inlet orifice 128, and when the key is positioned in the upper end of the key hole, as shown in FIG. 7, the two inlet orifices are aligned. Depending portion 140 includes an open bottom end.

Bottle cap 122 includes an inwardly extending, radial ring 64, and second component 118 includes an outwardly extending, radial lip 66. With bottle cap 122 completely threaded onto bottle stem 114, ring 64 is located below lip 66, as shown in shadow in FIG. 6. In this configuration, second inlet orifice 142 is out of alignment with first inlet orifice 128. As bottle cap 122 is unthreaded from bottle stem 114, friction between ring 64 and lip 66 causes second component 118 to move up relative to first component 116 until key 60 comes into contact with the top of key hole 62. Since second component 118 can move no further up, continued unthreading rotation of bottle cap 122 causes ring 64 to "snap" past (to move above) lip 66, so that the bottle cap can be completely removed from the bottle stem 114. With key 60 in contact with the upper surface of key hole 62, first inlet orifice 128 is aligned with second inlet orifice 142.

After using apparatus 110, bottle cap 122 is rethreaded onto bottle stem 114. At the start of this rethreading operation, ring 64 is located above lip 66. The rethreading rotation of bottle cap 122 and the friction between ring 64 and lip 66 causes second component 118 to move downwardly relative to first component 116 until key 60 contacts the first closed end 129. At this point first inlet orifice 128 is out of alignment with second inlet orifice 142. Continued rethreading rotation of bottle cap 122 onto bottle stem 114 causes ring 64 to "snap" past (to move below) lip 66 so that the bottle cap can be completely threaded onto the bottle stem, for storage between uses.

Alternative apparatus 110 functions in much the same way as does apparatus 10. For use, second inlet orifice 142 is positioned in alignment with first inlet orifice 128. Between uses and for storage or transportation, the inlet orifices are maintained in a non-aligned position.

FIGS. 9 and 10 illustrate a further embodiment of the present apparatus. This apparatus or bottle, shown generally at 210, includes a bottle body 212 which defines a receptacle 230, a bottle stem 214, a bottle cap 222 and a plurality of particles 220. Unless otherwise expressly stated, each of the components of the bottle 210, except for the plurality of particles 220, is made of a polymeric material which has no substantial detrimental affect on, and is not substantially detrimentally affected by, either the precursor aqueous liquid medium in bottle 210 or the chlorine dioxide-containing liquid medium dispensed by bottle 210. Also, the components of bottle 210 are sized in accordance with the same criteria used to size the components of bottle 10.

In bottle 210, bottle stem 214 includes an inner surface 270 which defines a chamber 272 in which the plurality of particles 120 is located. The floor or bottom side of chamber 272 is defined by a grid 274 which may be considered a series of inlet orifices each sized to permit free flow of precursor aqueous liquid medium and chlorine dioxide-containing liquid medium. However, the orifices of grid 274 are sufficiently small so as to prevent the particles 220 from escaping from chamber 272. Bottle stem 214 also includes a top portion 276 in which an outlet orifice 278 is located. Outlet orifice 278, which is the outlet of bottle 210, is sized to allow free flow of chlorine dioxide-containing liquid medium but is sufficiently small to prevent particles 220 from passing therethrough.

Grid 274 defines one side of a secondary chamber 280 and an orifice 282 provides a passage for precursor aqueous liquid medium from receptacle 230 to flow into secondary chamber 280. Orifice 282 is sized so that no liquid will flow through it without the imposition of an external force. Thus, even if bottle 210 was turned completely upside down so that outlet 278 were facing directly down, no liquid would flow through orifice 282. However, bottle body 212 is made sufficiently flexible so that a human user can squeeze bottle 212, exerting an external force on orifice 282. In this manner, liquid medium from receptacle 230 can be "forced" through orifice 282 into secondary chamber 280. Orifice 282 is located in a U-shaped element 284 which is adhered to ring 286, which is, in turn, adhered to the inner surface 288 of bottle 212. Orifice 282 can be replaced by a suitably configured porous membrane, a grid of micro-passages or orifices, or the like pressure barriers which function to prevent liquid from flowing from receptacle 230 into secondary chamber 280 without the imposition of external force, in particular hand pressure.

Bottle stem 214 includes an outer surface 290 which is threaded. Bottle cap 222 includes an inner surface 292 which is threaded. The threads of inner surface 292 and outer surface 290 matingly engage to secure bottle cap 222 onto bottle stem 214.

Bottle 210 functions as follows. When it is desired to store bottle 210 between uses, or during shipment, bottle cap 222 is threaded onto bottle stem 214 as shown in FIG. 9. When it is desired to deliver chlorine dioxide-containing liquid medium, bottle cap 222 is rotated and removed from bottle stem 214. The apparatus 210 is then turned over or on its side so that liquid from receptacle 230 is in contact with orifice 282. Bottle body 212 is hand squeezed to force precursor liquid from receptacle 230 to flow through orifice 282 into secondary chamber 280 and chamber 272 and, ultimately, through outlet orifice 278. As the liquid medium passes through chamber 220, it contacts the plurality of particles 120 which contacting effects the formation of chlorine dioxide. The chlorine dioxide-containing liquid medium from outlet orifice 278 is placed in a disinfection container, in particular a contact lens disinfection container.

After sufficient chlorine dioxide-containing liquid medium has been produced, the hand pressure on bottle body 212 is released and no further liquid passes through orifice 282. Once the apparatus 210 is uprighted, liquid from chamber 272 is drained through grid 274 into secondary chamber 280. At least some of the liquid in secondary chamber 280 flows through orifice 282 into receptacle 230. In this manner, the precursor aqueous liquid medium in receptacle 230 remains fresh and undiluted. The bottle cap 222 is threaded onto bottle stem 214 and the apparatus 210 is ready to be stored, and is available for further use in the future.

FIGS. 11, 12 and 13 illustrate an additional embodiment of the present chlorine dioxide delivery apparatus. This additional embodiment, shown generally at 310, includes a bottle body 312, a bottle stem 314, a membrane component 316., a distributor component 318, an outlet component 319, a bed of catalyst particles 320 and a bottle cap 322.

Each of the above-noted components of apparatus 310, except for the bed of particles 320, is made of a polymeric material which has no substantial detrimental effect on, and is not substantially detrimentally affected by, either the precursor aqueous liquid medium in apparatus 310 or the chlorine-dioxide containing liquid medium dispensed by apparatus 310. Each of the components of apparatus 310 can be sized appropriately to meet the requirements of the particular application involved. For example, bottle body 312 can be sized similarly to bottle body 12, discussed previously. Bottle body 312 is sufficiently flexible so that it can be squeezed by a human hand to exert a suitable amount of added pressure on the liquid in the bottle body 312.

Outlet component 319 includes an elongated outlet 324 through which liquid, in particular chlorine dioxide-containing liquid, can leave apparatus 310. A threaded surface 326 is provided on outlet component 319. Bottle stem 314 includes a threaded outer surface 328. The threads of threaded surface 326 can be intermeshed onto the threads of threaded outer surface 328 to secure outlet component 319 to bottle stem 314.

In addition, outlet component 319 includes a downwardly depending, inner support ring 330 which is positioned in substantially abutting relation to the inner wall 332 of bottle stem 314 when the outlet component is secured to the bottle stem. A series of downwardly extending ridges 334 are provided on surface 336 of outlet component 319. These ridges 334 help support catalyst bed 320 and to facilitate the flow of liquid to outlet 324.

Distributor component 318 is force fitted into inner support ring 330. Distributor component 318 includes a series of through holes 338 through which liquid can flow, and a series of upwardly extending ridges 340 which help support catalyst bed 320. Distributor component 318 also includes a centrally located, downwardly depending appendage 342 which terminates in a substantially rigid pin 344.

With distributor component 318 force fitted into outlet component 319, a chamber 346 is defined by the outlet component and the distributor component. Catalyst bed 320 is located within chamber 346. Catalyst bed 320 is quite shallow. That is, catalyst bed 320 is substantially more wide than it is deep, for example, on the order of at least about 5:1 or about 10:1 width to depth, to reduce the pressure drop across the bed. Filter elements 348 are located on either side of catalyst bed 320 and act to maintain the catalyst bed in place in chamber 346 and to prevent migration of the catalyst particles from the chamber. The filter elements 348 can be made of any suitable filter material. Each filter element contacts the ridges 334 or 340 one side of the catalyst bed 320. In this manner, catalyst bed 320 is adequately supported and maintained in place in chamber 346.

Membrane component 316 is force fitted into distributor component 318, and includes a flexible membrane 350 which has a central opening or orifice 351 into which rigid pin 344 fits when no deforming pressure is applied to the flexible membrane. When no deforming pressure is applied to flexible membrane 350, the combination of central orifice 351 and pin 344 acts to effectively prevent liquid from receptacle 331 from flowing past the flexible membrane. However, when a deforming pressure is applied to flexible membrane 350, the flexible membrane deforms and the membrane/pin combination allows liquid to flow past the flexible membrane, for example, into and through catalyst bed 320, as shown in FIG. 12. Over a limited range of deforming pressures, the liquid flow rate past membrane 350 is maintained constant within about 20% as the deforming pressure is varied. This "relatively constant liquid flow rate" feature is advantageous, for example, to allow a predictable and/or controlled rate of chlorine dioxide-containing liquid medium to be delivered by apparatus 310 independent of the deforming pressure applied.

Bottle cap 322, when in use, covers elongated outlet 324. The upwardly extending spout 352 of outlet component 319 includes an outwardly extending lip 354. Bottle cap 322 includes a downwardly depending, centrally located cup-like element 356 which includes a notch 358 sized and adapted to receive lip 354 of spout 352. With lip 354 received by notch 358, cap 322 is removably secured to outlet component 319. When it is desired to remove cap 322 from outlet component 319, human hand pressure is applied to bottle cap 322 to overcome the securing force of the combination of notch 358 and lip 354.

The particles within catalyst bed 320 include sufficient palladium to be effective to promote the conversion of a chlorine dioxide precursor in the precursor liquid which flows from receptacle 331 of bottle body 312 through the catalyst bed into chlorine dioxide, in particular a contact lens disinfecting amount of chlorine dioxide. These particles may be derived using any of a number of conventional techniques for depositing palladium on a substrate. The particles may be made of polymeric material or an inorganic oxide, such as alumina, silica and the like, and may be of substantially the same size or different sizes. The catalyst particles may have a size similar to that of granulated sugar. Particles of inert material may be interposed with the catalyst particles, for example, to dilute the catalyst bed and/or control the pressure drop through the catalyst bed, as desired.

Receptacle 331 includes a precursor aqueous liquid medium which may be, for example, similar to that described above with reference to the precursor aqueous liquid medium in receptacle 30.

The apparatus 310 functions as follows:

When it is desired to store the apparatus 310 between uses or during shipment, the apparatus is configured substantially as shown in FIG. 11. Thus, the rigid pin 344 substantially completely blocks the central opening in flexible membrane 350 and bottle cap 322 is secured to outlet component 319 to cover elongated outlet 324.

When it is desired to dispense chlorine dioxide-containing liquid medium from apparatus 310, for example, to disinfect a contact lens, the following procedure is implemented. Bottle cap 322 is removed from outlet component 319. Bottle body 312 is then tipped over so that liquid medium in receptacle 331 is in contact with the central opening of membrane 350. Human hand pressure is then applied to bottle body 312. This pressure causes membrane 350 to deflect, as shown in FIG. 12. This deflection allows a controlled amount of liquid from receptacle 331 to flow past flexible membrane 350. This liquid is then passed through through holes 338, through catalyst bed 320 and into elongated outlet 324 where it is dispensed. As the liquid passes through catalyst bed 320, chlorine dioxide generation is promoted so that the liquid exiting through elongated outlet 324 contains chlorine dioxide, in particular a contact lens disinfecting concentration of chlorine dioxide. The chlorine dioxide-containing liquid medium then passes from elongated outlet 324 into a lens container or other device where contact lens disinfection is to occur.

After sufficient chlorine dioxide-containing liquid medium has been delivered, the apparatus 310 is again uprighted and the hand pressure on bottle body 312 is ceased. Bottle cap 322 is then reapplied to outlet component 319. In this manner, the apparatus 310 is ready to be stored, and is available for further use in the future.

While this invention has been described with respect to various specific examples and embodiments, it is to be understood that the invention is not limited thereto and that it can be variously practiced within the scope of the following claims.

What is claimed is:

1. An apparatus for dispensing a liquid medium containing chlorine dioxide comprising:
   a reservoir defining a receptacle adapted for holding a precursor liquid medium having chlorine dioxide precursor therein; and
   a tip assembly into which the precursor liquid medium passes after the precursor liquid medium exits said receptacle, said tip assembly comprising:
   a chamber in which is located a promoter component effective to promote the generation of chlorine dioxide from the chlorine dioxide precursor in the liquid medium present in said chamber;
   an outlet providing a path for the liquid medium containing chlorine dioxide to exit said chamber; and
   isolation means acting to effectively separate the precursor liquid medium in said receptacle from said promoter component when it is desired that the precursor liquid medium in said receptacle be separated from said promoter component.

2. The apparatus of claim 1 wherein said isolation means includes a first component having a first inlet orifice in fluid communication with said receptacle, and a second component having a second inlet orifice in fluid communication with said chamber, said first component and said second component being moveable relative to each other so that said first and second inlet orifices are aligned to form a path for the precursor liquid medium to pass from said receptacle to said chamber, and said first and second orifices are non-aligned to effectively separate the precursor liquid medium in said receptacle from said promoter component.

3. The apparatus of claim 2 wherein said second component defines said outlet.

4. The apparatus of claim 2 wherein said second component is rotatable relative to said first component.

5. The apparatus of claim 4 which further comprises a stop assembly located on one or both of said first and second components and acting to limit the extent to which said second component is rotatable relative to said first component.

6. The apparatus of claim 4 wherein said second component includes a top surface, and said apparatus further comprises a cap adapted to be removably secured over said outlet and substantially surrounding said top surface of said second component, said cap being adapted so as to contact said top surface of said second component so that said second component rotates in response to rotation of said cap.

7. The apparatus of claim 2 wherein said second component is moveable along its longitudinal axis relative to said first component.

8. The apparatus of claim 7 which further comprises a restrictor assembly located on one or both of said first and second components and acting to restrict the movement of said second component along its longitudinal axis relative to said first component.

9. The apparatus of claim 2 wherein said reservoir includes an outlet port in which at least a portion of said first component and said second component are located.

10. The apparatus of claim 9 wherein said outlet port of said reservoir includes an outer surface which is threaded, and said apparatus further comprises a cap adapted to be removably threaded onto said outer surface of said outlet port to effectively cover said outlet.

11. The apparatus of claim 2 wherein said promoter component includes a plurality of particles.

12. The apparatus of claim 1 wherein said promoter component includes a transition metal component in an amount effective to promote the generation of a contact lens disinfecting amount of chlorine dioxide from the precursor liquid medium present in said chamber.

13. The apparatus of claim 12 wherein said transition metal component is selected from the group consisting of platinum components, palladium components, ruthenium components and mixtures thereof.

14. The apparatus of claim 12 wherein said transition metal component is selected from the group consisting of palladium components and mixtures thereof.

15. The apparatus of claim 1 wherein said isolation means includes at least one orifice in fluid communication with said receptacle and said chamber, said at least one orifice being such as to prevent the flow of precursor liquid medium from said receptacle therethrough when said at least one orifice is subjected to only liquid pressure from the precursor liquid medium in said receptacle.

16. The apparatus of claim 15 wherein said reservoir is flexible and said at least one orifice is structured so that upon application of hand pressure to said reservoir and liquid pressure from the precursor liquid in said receptacle to said at least one orifice, precursor liquid medium from said receptacle is caused to pass through said at least one orifice.

17. The apparatus of claim 15 which further comprises a secondary chamber in fluid communication with both said chamber and said at least one orifice, said secondary chamber having a diameter larger than that of said at least one orifice, and being substantially free of said promoter component.

18. The apparatus of claim 17 which further comprises an inlet in fluid communication with both said chamber and said secondary chamber and being structured to allow free flow of liquid medium between said chamber and said secondary chamber.

19. The apparatus of claim 18 wherein said inlet includes a plurality of flow orifices each of which being sized sufficiently large to allow free flow of liquid medium between said chamber and said secondary chamber.

20. The apparatus of claim 15 wherein said promoter component includes a plurality of particles.

21. The apparatus of claim 15 wherein said promoter component includes a transition metal component selected from the group consisting of platinum components, palladium components, ruthenium components and mixtures thereof.

22. The apparatus of claim 1 wherein said promoter component is held substantially stationary in said chamber.

23. The apparatus of claim 1 wherein said isolation means includes a flexible membrane which is deformable by the application of deforming pressure thereto and which is located between said receptacle and said chamber and includes an orifice therethrough, and a rigid pin-like element substantially stationary relative to said chamber and extending into said orifice when no deforming pressure is applied to said membrane to effectively prevent or substantially inhibit precursor liquid medium from said receptacle from passing said membrane, said membrane and pin-like element being adapted to allow precursor liquid medium from said receptacle to pass said membrane when a deforming pressure is applied to said membrane.

24. The apparatus of claim 23 wherein said membrane and said pin-like element are structured so that the flow rate of precursor liquid medium past said membrane is maintained relatively constant as said deforming pressure is varied over at least a limited range of deforming pressures.

25. The apparatus of claim 23 wherein said promoter component is located in a bed of particles.

26. The apparatus of claim 25 wherein said bed of particles is substantially more wide than deep.

27. The apparatus of claim 25 which further comprises at least one filter element in contact with said bed of particles and acting to hold said bed of particles in place of said chamber.

28. The apparatus of claim 25 which further comprises a distributor component structured and adapted to facilitate the flow of precursor liquid medium from said receptacle through said bed of particles.

29. The apparatus of claim 28 wherein said distributor component and said pin-like element are included in the same part.

30. The apparatus of claim 23 wherein said transition promoter composition includes a metal component selected from the group consisting of platinum components, palladium components, ruthenium components and mixtures thereof.

* * * * *